United States Patent [19]

Kleinberg et al.

[11] Patent Number: 4,598,710
[45] Date of Patent: Jul. 8, 1986

[54] SURGICAL INSTRUMENT AND METHOD OF MAKING SAME

[75] Inventors: Larry K. Kleinberg, Burbank; Donald S. Evans, Pasadena, both of Calif.

[73] Assignee: Urban Engineering Company, Inc., Burbank, Calif.

[21] Appl. No.: 572,236

[22] Filed: Jan. 20, 1984

[51] Int. Cl.[4] .............................................. A61B 17/32
[52] U.S. Cl. .................................... 128/318; 128/305; 128/751; 30/290
[58] Field of Search ............... 128/304, 305, 276, 307, 128/309, 312, 751-755, 757, 758, 318; 30/290

[56] References Cited

U.S. PATENT DOCUMENTS

| 3,173,414 | 3/1965 | Guillant | 128/318 |
| 4,111,207 | 9/1978 | Seiler, Jr. | 128/305 |
| 4,274,414 | 6/1981 | Johnson et al. | 128/305 |
| 4,461,305 | 7/1984 | Cibley | 128/305 |

FOREIGN PATENT DOCUMENTS

| 3035416 | 6/1982 | Fed. Rep. of Germany | 128/305 |
| 8101363 | 9/1981 | PCT Int'l Appl. | 128/305 |
| 8103122 | 11/1981 | PCT Int'l Appl. | 128/318 |
| 2018601 | 10/1979 | United Kingdom | 128/305 |

Primary Examiner—John F. Niebling
Assistant Examiner—Terryence Chapman
Attorney, Agent, or Firm—Frank L. Zugelter

[57] ABSTRACT

A surgical instrument comprising a pair of co-axially assembled tubes having their distal walls in bearing relationship and with registrable openings extending through such distal end and annular walls correspondingly joined to their respective distal walls. The inner tube reversibly rotates within its matched outer tube in operation of the invention, as action by cutting edges formed about such openings severs tissue drawn into the inner tube by suction. Each distal end wall includes a pair of circular cutting edges, those in the inner tube having a straight cut across its thickness while those in the outer tube have a full radiused cut across its thickness. Full radiused cuts across the thicknesses of the annular walls of the inner and outer tubes are provided for arcuately-formed and parallel cutting edges forming the respective openings in these tubes in their annular walls. A method to form these openings by means of these cutting edges is disclosed.

6 Claims, 21 Drawing Figures

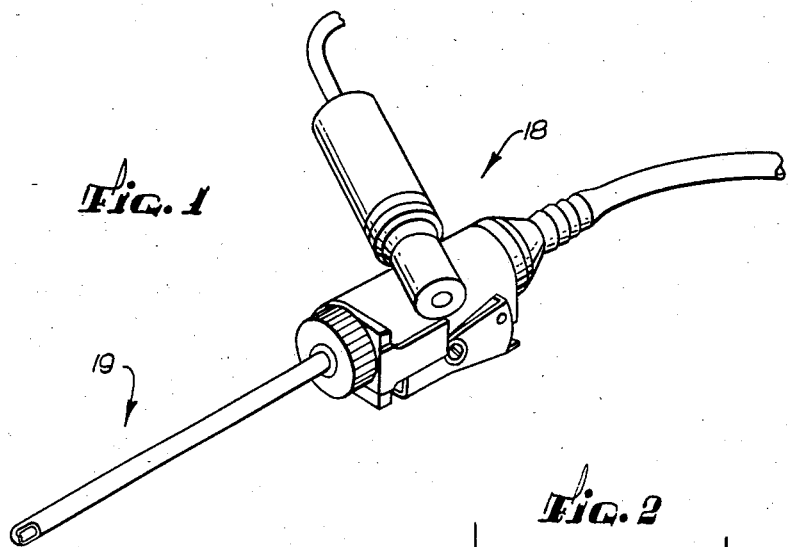
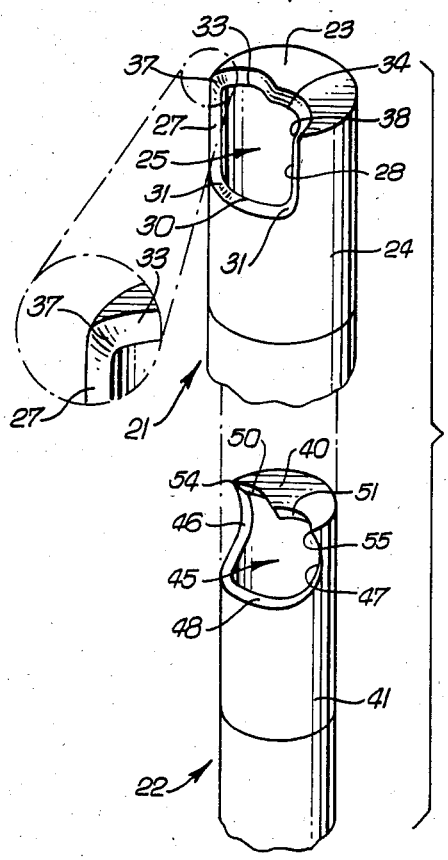
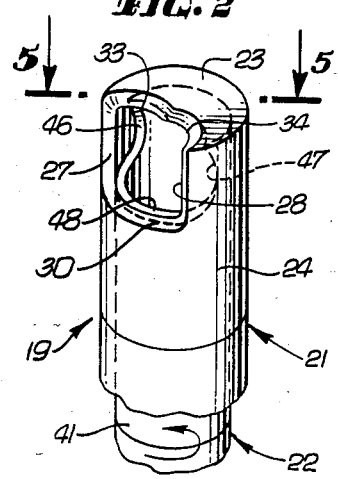
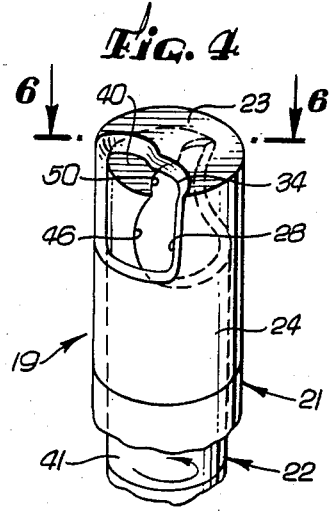

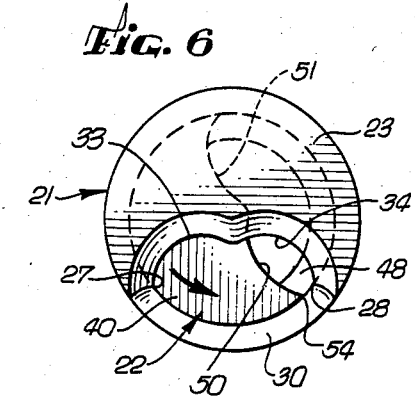
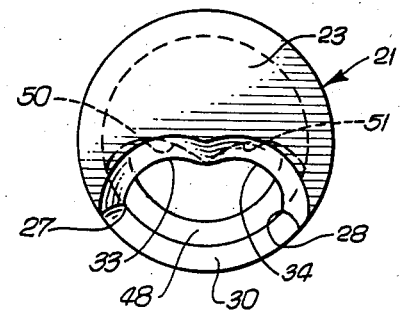
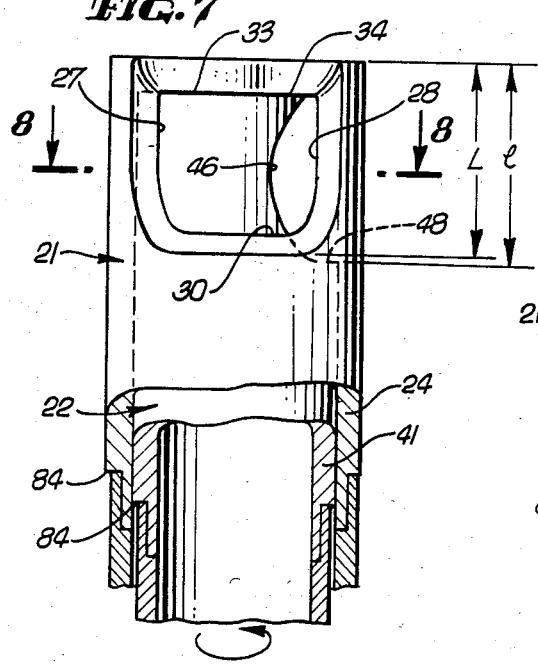
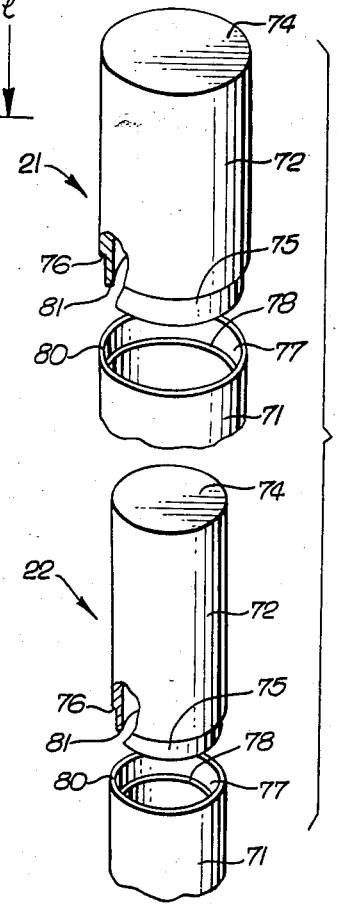
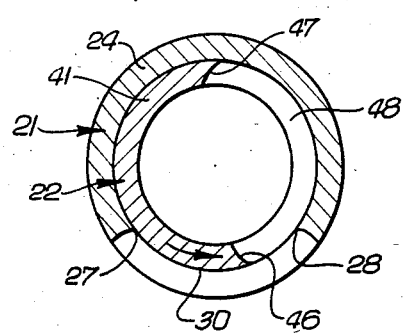

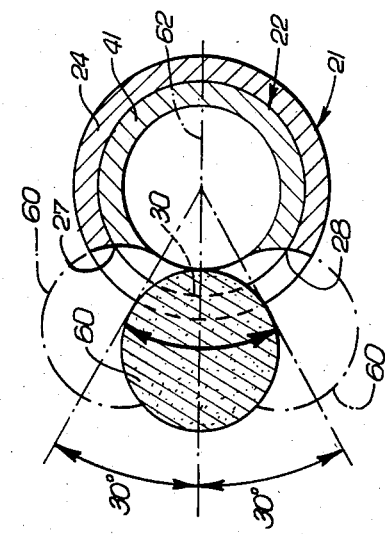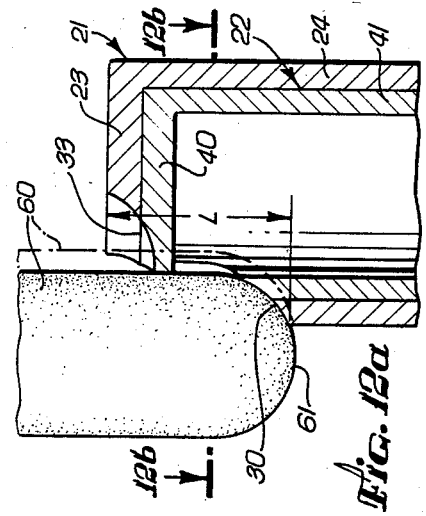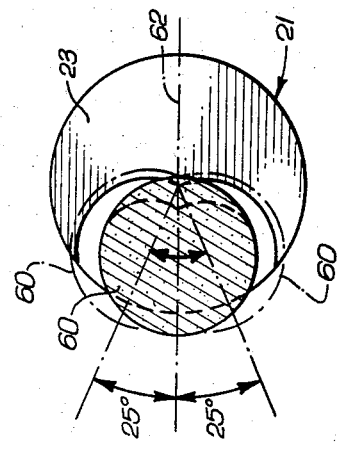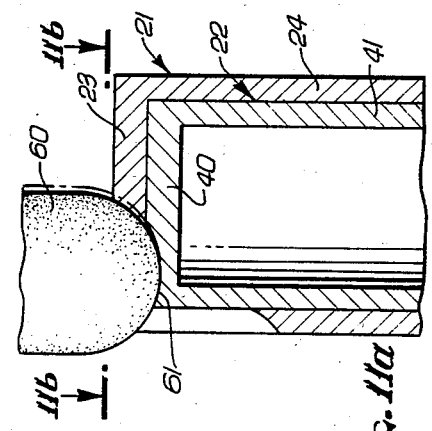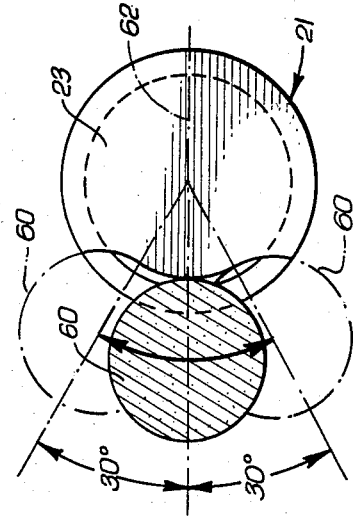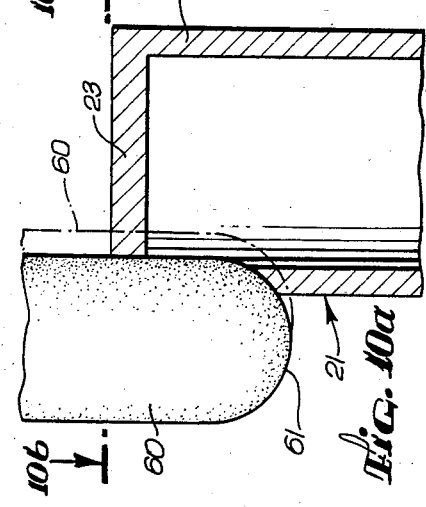

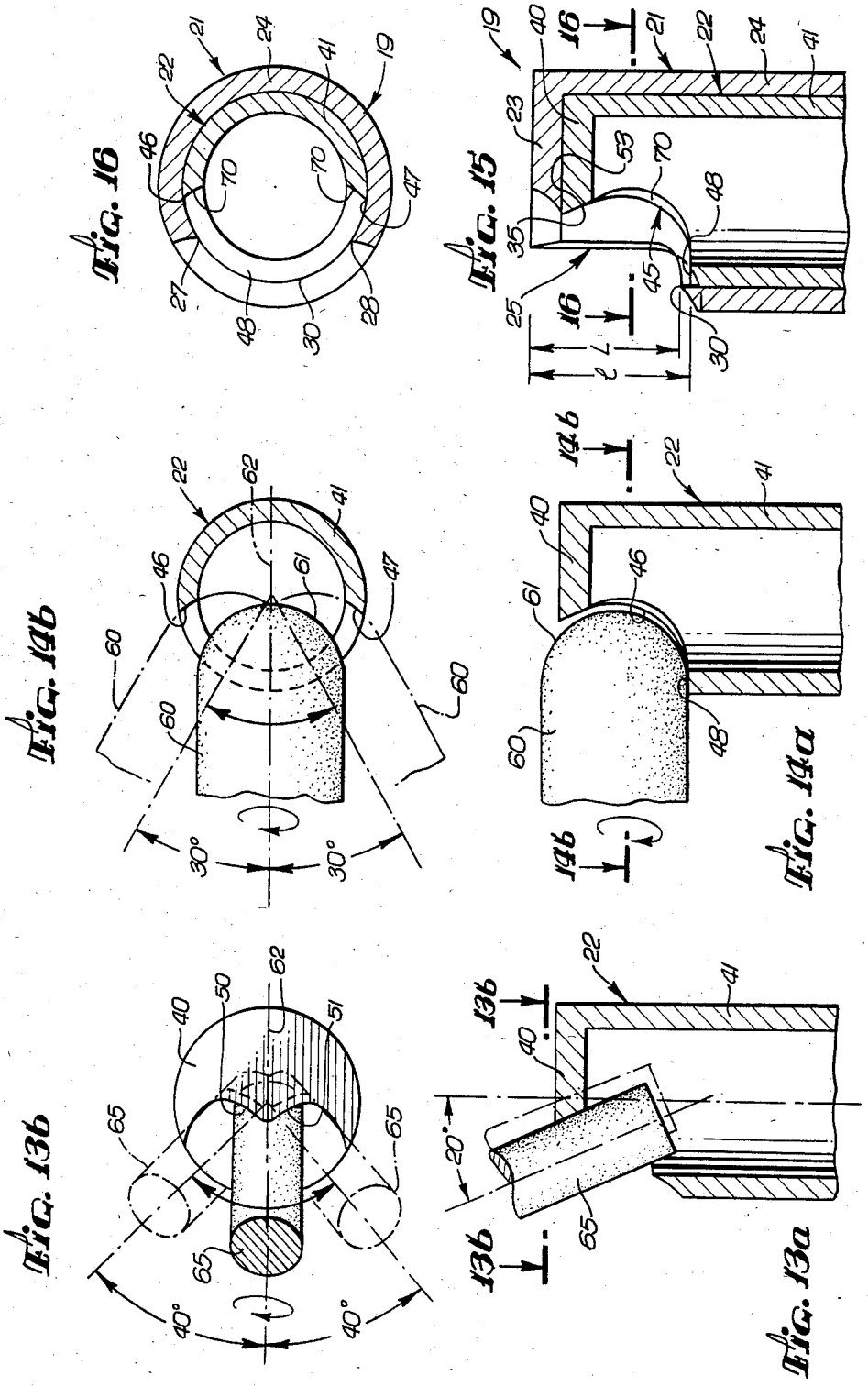

SURGICAL INSTRUMENT AND METHOD OF MAKING SAME

TECHNICAL FIELD

This invention is directed to a surgical instrument of the remote cutting type, in which cutting edges on an inner tubular member cooperate with cutting edges on an outer tubular member while vacuum or suction is applied through the instrument to the cutting site at which tissue or other substances are to be severed and withdrawn through the instrument as cutting action continues.

BACKGROUND ART

Efforts in the field are represented in the following prior art teachings: U.S. Pat. Nos. 737,293; 1,493,240; 1,585,934; 1,663,761; 2,369,925; 3,618,611; 3,732,858; 3,734,099; 3,844,272; 4,203,444; 4,274,414.

Generally, the state-of-the-art discloses coaxial inner and outer tubes constituting a surgical instrument, and which include cooperating cutting edges in distal end and side or annular walls, the inner tube being rotatably driven while the outer tube remains stationary. Means to maintain fluid flow from these cutting regions through the instrument's inner tube also is known in the art, thereby creating a way to draw or pull material through openings formed by such cutting edges to be severed.

DISCLOSURE OF THE INVENTION

The invention is embodied in a surgical instrument comrising a pair of co-axially assembled tubes, operatively connectable to a driving unit, their distal end walls being in bearing engagement with one another and having registrable openings extending through the distal end and annular walls forming the instrument, and further uniquely identified by a pair of circular cutting edges in each of the distal end walls, arcuately-formed cutting edges in the annular wall of the inner tube, and spaced parallel cutting edges in the annular wall of the outer tube, all of such edges developed in body formations in the tubes forming such openings.

Further, a full radiused cut across the thicknesses of the annular walls forming the spaced parallel cutting edges, the arcuate cutting edges and the pair of circular cutting edges in the distal end wall of the outer tube and a straight cut across the thickness of the pair of circular cutting edges in the inner tube assure positive cutting angles in the cooperative action of edges severing material, irrespective of the direction of rotation of the inner tube relative to its outer tube. As the inner member rotates its opening beyond or past the opening in its outer member, with these positive cutting angles for their respective cutting edges, an effacacious scissors action occurs on the tissue or other material drawn into such openings that extend into both annular and distal end wall configurations of the instrument.

Prior art instruments do not include positive cutting angles across the thicknesses of the walls for the openings in the inner and outer tube members. Nor does the prior art teach or suggest the incorporation of pairs of circular cutting edges cooperatively related in the distal end walls of the tubes. Such incoporation provides additional cutting edge areas not heretofore realized in this type of surgical cutting instrument.

The method by which these cutting edges are generated within the instrument is likewise unique and novel, particularly in view of the small dimensions of these tubes. For example, the O.D. of the outer tube is 0.166 inch, its wall thickness being 0.017 inch. The O.D. for the inner tube is on the order of 0.1335 inch, its wall thickness on the order of 0.013 inch. The thickness of the distal end wall is in the order of 0.020 inch. Generating positive cutting angles in this size of surgical instrument has not materialized to date, much less in a manufacture including additional cutting area in the distal end walls of the instrument.

An object of this invention is to provide a novel surgical cutting instrument and a novel method of making same.

A further object of this invention is to provide positive cuts across the thicknesses of tubular walls in which cutting edges forming openings therein are generated.

Another object of this invention is to produce a clean scissors action on tissues and other substances in the body to which the instrument is applied, by the cooperation of unique cutting edges generated in inner and outer tubular members of the surgical instrument.

Another object of the invention is to provide additional cutting area in the distal walls of tubular members while maintaining central bearing engagement therebetween.

These and other objects and advantages of the invention will become more apparent upon a complete and full reading of the following description, appended claims thereto, and accompanying drawing comprising four (4) sheets of 16 FIGURES.

BRIEF DESCRIPTION OF THE DRAWING

FIG. 1 is a perspective view of an apparatus in which subject matter embodying this invention is employed.

FIG. 2 is a perspective view of a surgical cutting instrument in which the invention is embodied.

FIG. 3 is an exploded perspective view of the two members shown in FIG. 2, with an exploded bubble of a small portion shown in FIG. 3.

FIG. 4 is a perspective view of the subject matter of FIG. 2, with the inner member rotated relative to the outer member.

FIG. 5 is a view taken on line 5—5 of FIG. 2.

FIG. 6 is a view taken on line 6—6 of FIG. 4.

FIG. 7 is an elevational view of the perspective of FIG. 4.

FIG. 8 is a view taken on line 8—8 of FIG. 7.

FIG. 9 is an exploded perspective view of outer and inner tubular members of the previous FIGURES, prior to formation of cutting edges on such members.

FIGS. 10a and 10b are elevational and end views, respectively, partly in section, exemplifying the manner by which an initial opening in the outer tubular member in made.

FIGS. 11a and 11b are elevational and end views, respectively, partly in section, exemplifying the manner by which the end wall of the outer member is ground to form an opening therein, while penetrating the end wall of the inner tubular member.

FIGS. 12a and 12b are sectional views, elevational and plan, respectively, exemplifying the manner by which cutting edges opposing each other in the annular wall adjacent the top wall in the outer tubular member are completed, while providing a partial or initial opening in the annular wall of the inner tubular member adjacent its top wall.

FIG. 13a is an elevational view, partly in section, across the center line of the inner tubular member, exemplifying the manner of penetrating, by grinding, its top wall in a positive cut direction and to a desired point alone such center line of the tubular member.

FIG. 13b is a view taken on line 13b—13b of FIG. 13a, phantom lines exemplifying the manner of relative rotation between the grinding burr and the top wall of the inner tubular member to produce cutting edges along separate arcs generated in the top wall.

FIG. 14a is an elevational view, partly in section, across a center line for the inner tubular member, exemplifying the manner of penetrating, by grinding, its annular wall.

FIG. 14b is a view taken on line 14b—14b of FIG. 14a, phantom lines exemplifying the manner of relative rotation between the grinding burr and the annular wall adjacent the end wall of the inner tubular member to produce opposing arcuate cutting edges across the width of the opening generated in such member.

FIG. 15 is an elevational section view showing a matched set of tubular members embodying the invention.

FIG. 16 is a view taken on line 16—16 of FIG. 15, showing in particular the positive cutting angle of the inner tube's annular wall edges in relation to the cutting edges on the annular wall of the outer member.

BEST MODE(S) FOR CARRYING OUT THE INVENTION

Referring now to the drawing wherein reference characters correspond to like numerals hereinafter, FIG. 1 discloses an apparatus 18 to which the surgical instrument 19 of this invention is operatively connected. Apparatus 18 is of the kind disclosed in U.S. Pat. No. 3,618,611 and it, along with operative connection of instrument 19 thereto, is not part of the instant invention. However, it is apparent that instrument 19 is readily adaptable to such apparatus 18 with which it works in actual practice.

Instrument 19 generally comprises an outer tube 21 and a tube 22 assembled within tube 21, FIGS. 2, 3, 4. Outer tube 21 comprises distal end wall 23 joined to side or annular wall 24 which extends from the distal end of tube 21 in a proximal direction to be operatively connected to apparatus 18, FIG. 1. An opening 25 is formed in outer tube 21 by body formation found in both side wall 24 and end wall 23. Such body formation in side wall 24 comprises a pair of spaced parallel and longitudinally-disposed cutting edges 27,28, each having a radiused cut across its wall's thickness and each opposing the other across the width of opening 25, and which are joined together by an edge 30 disposed circumferentially around annular wall 24 at a chosen length L, FIGS. 7, 15, from the distal end of tube 21. Circumferential edge 30 at its opposing extremities flows into or joins corresponding cornered cutting edge portions 31, each having a radiused cut across its thickness, and which in turn flow into or join their corresponding cutting edges 27, 28.

The body formation for opening 25 which is found in end wall 23 at the distal end of tube 21 comprises a pair of cutting edges 33, 34, each circular in form, and each having a radiused cut across its wall's thickness. Circular cutting edges 33, 34 are joined at their contiguous extremities generally centrally of the area of end wall 23, their juncture lying, as viewed from the direction of opening 25, before a protrusion of a bearing surface 35, situated on the interior surface of distal end wall 23, between the tube's axis and opening 25. The other or opposing extremities of cutting edges 33, 34 correspondingly join longitudinally-diposed edges 27, 28, respectively, in annular wall 24, best seen in FIG. 3, and identified as junctures 37, 38, respectively. It is to be noted that each juncture 37, 38 is not a sharp point of juncture, as shown in the bubble blow-up attached to FIG. 3, but rather is a non-sharp juncture to prevent undesirable catching of tissue by outer tube 21 as it is inserted into or otherwise functioning within a body orifice or hole into which the surgical instrument 19 has been introduced. Each non-sharp juncture 37, 38 is formed by rounding off in two planes the otherwise sharp corner produced in the manufacturing steps for outer tube 21.

The inner tube 22 comprises a distal end wall 40 joined to a side or annular wall 41 which extends from the distal end of such tube 22 in a proximal direction to be operatively connected to apparatus 18, FIG. 1. An opening 45 is formed in inner tube 22 by body formation found in both side wall 41 and end wall 40. Such body formation in side wall 41 comprises a pair of spaced longitudinally-disposed circular or arcuate cutting edges 46, 47, each having a radiused cut across its wall's thickness, and each opposing the other across the width of opening 45, and which are joined by an edge 48 disposed circumferentially around annular wall 41 at a chosen length 1, FIGS. 7, 15, from the distal end of outer tube 21. Circumferential edge 48 flows at its opposing extremities directly into corresponding spaced arcuate cutting edges 46, 47, best seen in FIG. 3.

In operation, FIGS. 2, 4, 6, 7, 8 illustrate that cutting action occurs by the cooperative action between cutting edges of both tubes, as inner tube 22 rotates within its outer tube 21. In particular, as inner tube 22 rotates in the direction of the arrow, FIGS. 2, 4, 6, as outer tube 21 remains stationary, the arcuate edge configuration 46 in side wall 41 of inner tube 22, FIGS. 4, 7 cooperates in cutting action with the outer tube's cutting edges 31, 28, in its side wall 24, while a scissors-like cutting action simultaneously takes place between circular cutting edge 50 in end wall 40 of inner tube 22 with circular cutting edge 34 in end wall 23 of outer tube 21. It may be noted that the cutting point on tissue-being-severed by the cooperating edges 50, 34 continues to move away from the center of both tubes 21, 22 as inner tube 22 continues to rotate within and relative to outer tube 21. In other words, the same moving action is occurring here along the cutting edges 50, 34 on the distal ends 40, 23 of tubes 22, 21 as occurs when a conventional scissors effectively cuts a sheet of paper in two.

In reverse rotation of inner tube 22 in outer tube 21, arcuate edge configuration 47 in side wall 41 of inner tube 22 cooperates with the outer tube's cutting edges 31, 27 in its side wall 24, while a scissors-like cutting action simultaneously takes place between circular cutting edge 51 in end wall 40 of inner tube 22 with circular cutting edge 33 in end wall 23 of outer tube 21.

In terms of assembly and operation of instrument 19 when operatively connected to apparatus 18, FIG. 1, reference to the disclosure of U.S. Pat. No. 3,618,611 shows how tubes 21, 22 can be operatively connected thereto. Such disclosure also shows how a vacuum is applied, which is also applicable here, through an inner tube to openings for withdrawing severed material through the inner tube.

It is to be noted that length 1 for opening 45 of inner tube 22 is longer than length L for opening 25 of outer tube 21, FIGS. 2, 4, 7. Measurement for the lengths or depths of openings 25, 45 may, of course, be taken from other than distal end 23 on outer tube 21.

The body formation for opening 45 which is found in distal end wall 40 of inner tube 22 comprises a pair of cutting edges 50, 51, each circular in form and each having a straight cut across its wall's thickness. Cutting edges 50, 51 are joined at their contiguous extremities generally centrally of the area of distal end wall 40, their juncture lying, as viewed from the direction of opening 45, before a protrusion of a bearing surface 53, FIG. 15, situated on the exterior surface of distal end wall 40, between the tube's axis and opening 45. The other or opposing extremities of circular cutting edges 50, 51 correspondingly join arcuate cutting edges 46, 47, respectively, in annular wall 41, best seen in FIG. 3, their junctures 54, 55 defining correspondingly sharp points.

Inner tube 22 is co-axially assembled to outer tube 21, FIGS. 2, 3, 4, 7, with a slip fit occurring between the tubes. Openings 25, 45 register with one another in one position, FIG. 2, however, the cutting edges on inner tube 22 do not, in such registration, register with the cutting edges of outer tube 21, FIGS. 2, 5. End wall 40 of inner tube 22 engages end wall 23 of outer tube 21. By reason of longitudinal pressure exerted by apparatus or drive unit 18 in the operative connection of instrument 19 thereto, bearing surfaces 35, 53. FIG. 15, engage and cooperate with each other for any relative position for tubes 21, 22 and their openings 25, 45. Any air separation or gap is prevented and which otherwise would cause pinching of tissue. The noted protrusions of bearing surfaces 35, 53 prevent ejection of inner tube 22 through the distal wall opening in outer tube 21. Note in FIGS. 4, 6 that inner tube 22 is rotated approximately 120° relative to outer tube 21 over their registered positions shown in FIGS. 2, 5, and the bearing surfaces 35, 53 nevertheless remain engaged in co-operative relationship. This relationship continues throughout full rotation of inner tube 22 within outer tube 21, in their assembly to one another.

Method of Making

Referring now to FIG. 10 et seq., and the following description, a method which generates cutting edges on the body formation of tubes 21, 22 forming their respective openings 25, 45 is disclosed.

The outer tube 21 is first secured in a suitable fixture with its distal end 23 sufficiently projecting therefrom so that a diamond-impregnated burr or mandril 60, with a full radiused end 61, can axially travel or displace in a lineal (distal to proximal) direction, perpendicularly to a center line 62 for both tube and burr, to initiate an opening in both the end and side walls of tube 21, FIGS. 10a, 10b. Burr 60 is moved longitudinally and in parallel relationship to the axis of the tube. A small portion of the distal end wall 23 is ground away while the rotating grinding surface of burr 60 grinds upon its adjacent side or annular wall 24, FIG. 10a. As burr 60 is being fed in slowly, it also is revolved or oscillated 30° about the tube's axis, to each side of center line 62, FIG. 10b, to develop cutting edges 27, 28 across the width of opening 25. Burr 60 continues to be fed axially to the desired axial depth L for opening 25 in outer tube 21. Burr 60 then is removed.

Referring now to FIGS. 11a, 11b, inner tube 22 is inserted into outer tube 21 so that their corresponding end walls 40, 23 engage each other, FIG. 11a. The tubes 21, 22 now are locked together in this position by suitable means (their lengths to their proximal ends being different) at their proximal ends. Burr 60 is fed axially upon such tubes, from their distal ends towards their proximal ends, and perpendicular to center line 62 for both burr and tubes. The radiused end 61 on burr 60 fully penetrates through the outer tube's end wall 23, FIG. 11a. The thickness of the inner tube's distal end 40, FIG. 11a, is but partially penetrated by the radiused end 61 of burr 60. [This partial penetration in its distal wall 40 can be readily observed in FIG. 12a.] It is important to note that the full radius of burr 60 is not utilized in the penetration of either distal end 40, 23 of the tubes, but rather only the radii on the radiused end 61 of burr 60 is utilized. In this manner, the bearing surface 35, FIG. 15, on the outer tube's distal end 23 is formed in an area on and around its axis in a general direction extending to the opening already generated in its side wall 24.

Now, burr 60 is revolved 25° about the coincident axes of both tubes, to each side of center line 62, FIG. 11b. It is to be noted here that the apex of such 25° angles lies on the axes for the tubes. However, the radiused end 61 (on burr 60), and not the full radius of burr 60, is generating the cut through the outer tube's distal end 23. Thus, the bearing surface 35, FIG. 15, on the interior surface of distal end 23 is not cut away (bearing 35 is in FIG. 11a, but not referenced). In these revolutions of mandril 60 about both tubes, the pair of cutting edges 33, 34 in the outer tube's distal wall 23 are generated, as a result of the cut made by radiused end 61 (on burr 60), in addition to generating bearing surface 35 for distal end 23.

Referring now to FIGS. 12a and 12b, the axial position of burr 60 is moved radially outwardly along center line 62, to a position for generating an initial cut in side wall 41 of inner tube 22, corresponding to a disposition which registers with the cut generated by burr 60 for side wall 24 of outer tube 21 (FIGS. 10a, 10b) and to finish grind the edges 27, 28, 30 and 31 in side wall 24 of outer tube 21.

Rotating burr 60 is fed or translated axially, in a proximal direction, as it also is being revolved 30° about the axes of the tubes, to each side of center line 62, FIGS. 12a, 12b. Such revolutions generate the cuts at the desired width of opening 25 and develop the configurations for cutting edges 27, 28 in side wall 24 of outer tube 21. Upon reaching the desired depth L, the edge 30 and cutting edges 31 in side wall 24 are generated. The full configuration of opening 25, which extends into both the distal and side walls of outer tube 21, now is formed, while a mininal opening in side wall 41 of inner tube 22 has been generated.

Tubes 21, 22 now are separated. The following or subsequent grinding steps are performed on end wall 40 and annular wall 41 of inner tube 22 to provide finished cutting edges therein for effacacious cutting action with cooperating edges on outer member 21.

Referring now to FIGS. 13a, 13b, a rotating straight burr or mandril 65 approximating one half the diameter of burr 60 is utilized. Inner tube 22 is secured in a suitable fixture and burr 65 is slowly introduced at a 20° angle to the axis of tube 22 into its minimal opening in both distal and annular walls respectively formed in the steps illustrated in FIGS. 10a, 10b and in FIGS. 12a, 12b, along center line 62 which lies in the plane containing the axes of burr and tube. As burr 65 travels in and out in a direction corresponding to its axis, the 20° angle of linear travel effects a positive cut or cutting angle across the thickness of end wall 40. It also is being fed in a (horizontal) direction towards the axis of tube 22, FIG. 13a, until a desired point of cut is reached. This desired point of cut is measured along a diameter for distal wall 40 coincident upon center line 62 (FIG. 13b) and equals the radius for wall 40 plus a distance, extending towards opening 45 for tube 22, mounting to a desired dimension for bearing surface 53 on distal wall 40. Only then, as observed in FIG. 13b, is burr 65 revolved 40° about the axis of tube 22, to each side of such plane in order to generate a positive cut or cutting angle across the thickness in distal wall 40 throughout the arcs of cutting edges 50, 51, while retaining its bearing surface 53, FIG. 15, situated about the axis of inner tube 22. End wall 40 on inner tube 22 now includes a positive cutting angle in each of its pair of circular cutting edges 50, 51, across their respective thicknesses.

Referring now to FIGS. 14a, 14b, a finished cut on the opposing arcuate edges 46, 47 for opening 45 in side wall 41 of inner tube 22 is generated. Burr 60, with its full radiused end 61, is used. Inner tube 22 is secured in a suitable fixture. Burr 60 is introduced into the minimal opening existing in side wall 41, at a right angle to the axis of the tube, FIG. 14a. The full radius of rotating burr 60 is brought to bear to produce circumferential edge 48 at the desired depth 1, measured from the distal end 23 of outer tube 21. As burr 60 advances radially inwardly of side wall 41 of tube 22, its radiused end 61 does not make contact with distal wall 40, FIG. 14a, in this step. However, layers of radiused end 61 establish the location of arcuate cuttingedges 46, 47 and generate a positive cut or cutting angle across the thicknesses of such edges 46, 47 as burr 60 is revolved 30° about the axis of tube 22, to each side of center line 62, FIG. 14b.

FIGS. 15, 16 illustrate the finished surgical instrument 19. A positive cutting angle 70 may be observed across the thickness of arcuate edges 46, 47, FIG. 16, Circumferential edge 48 on inner tube 22 lies at or below edge 30 on side wall 24 of outer tube 21. Although edge 30 is shown in FIG. 15 not to be a parallel cut across the thickness of annular wall 24, it tends to become so parallel, during FIG. 12b manipulation of burr 60 to each side of center line 62. In any event, edge 30 does not substantially contribute to the cutting functions performed by other cutting edges in instrument 19.

FIGS. 15, 16 also illustrate a matched set of tubes 21, 22, which is produced after a de-burring of metal fragments takes place separately with each of such tubes. The bearing surfaces 35, 53 are in complementing engagement in the assembly of each matched set, an important advantage over prior-art like surgical instruments. Also, additional area of cutting edges is achieved by the pairs of circular cutting edges, 50 with 34 and 51 with 33, cooperating in the distal end walls 23, 40 of the tubes.

Various changes and modifications can be made in the method. For example, referring to FIGS. 11a, 11b, the generation of the portion of opening 25 lying in distal end wall 23 of outer tube 21 in this step may be performed without being locked together with inner tube 22. Nor is it necessary to cause partial penetration of distal end wall 40 of inner tube 22 by locking the latter to outer tube 21. Each of these penetrations can be performed on each of the tubes 21, 22 separately.

In a manually-operated jig set-up, the tubes 21, 22 are caused to rotate in each step into either rotating burr 60, 65 as the latter is caused to reciprocate in a plane while being mounted on a movable carriage. The axes of the burrs are maintained in a plane initially with center line 62, while the tubes are revolved the indicated angular oscillations to obtain the desired cuts at their desired locations. Stop blocks are mounted on the movable carriage to limit linear (arcuate) travel of the burrs and radial travel for burr 65, while stop pins and adjusting screws (functioning as stops) are mounted to the fixture to limit rotation of the tubes. These matters are known expedients in machine-shop practice.

In manual practice, a Dremel motor drives burr 60 (0.110 inch dia.) and burr 65 (0.055 inch dia.) at 28,000 rpm to provide the grinding force to make the cuts across the thicknesses of the distal end and annular walls, of tubes constituting instrument 19 which embodies the invention. 35,000–50,000 rpms is preferable, however.

The practice of the invention also can be carried out on a numerically-controlled [NC] machine wherein the burrs 60, 65 are revolved about stationarily-disposed tubes 21, 22.

Each set of completed or finished tubes 21, 22 should remain together as a matched set. Lapping and polishing of each set is suggested after its tubes are manufactured in accordance with the principles and means of this invention described herein.

It should be noted that openings 25, 45 should not be any wider or longer than the unit area within the dimensions of inner tube 22, as only severed material not exceeding such unit area should flow through inner tube 22 as the result of suction applied by, say, apparatus 18. For example, with the dimensions of the tubes described herein, $1 = 0.115$ inch and $L = 0.110$ inch.

Concerning the formation of rounded junctions 37, 38, FIG. 3, a ceramic stone may be used to round off, by hand, what otherwise would remain to be sharp points or junctures. Rounding off in two different planes removes any sharpness.

Formation of Tubes 21, 22

Reference to FIG. 9 and this description provides disclosure of the formation of each of tubes 21, 22 prior to manufacturing surgical instrument 19. It should be noted that the same reference characters in FIG. 9 have been adopted to identify the elements forming inner tube 22 as is adopted for the elements forming outer tube 21, as the formation for both tubes is the same. Only their sizes are different.

First, a tube 71 and a tip member 72 are bored out in separate conventional machining operations, to form their respective inner wall dimensions, which are substantially the same. However, an end wall dimension 74 remains on tip member 72 after its boring or blank-out machining operation is completed. Thereafter, the outside diameter of tip member 72 is reduced along a length as at 75, terminating at a shoulder 76, and then cut to its final length. To accomodate in member 71 the smaller dimension 75 of tip member 72, the end of member 71 is bored out, as at inner wall 77, for fitting thereto the reduced outer dimension of wall 75. The end of wall 75 seats upon a shoulder 78 in member 71 formed as a result of boring inner wall of dimension 77, while wall 75 itself slip fits to wall 77. As these members slip fit to one another, the shoulder 76 formed by reduced dimension 75 seats upon or engages annular end 80 of member 71, while annular end 81 of element 72 seats on shoulder 78 of member 71. The resulting fit of members 71, 72 is illustrated by a line of juncture 84, FIG. 7, where end 80 and shoulder 76 meet.

Prior to securely fitting tip member 72 to member 71, member 72 is heat treated to a Rockwell hardness of 53 to 56, as cutting action for surgical operations requires such hardness. Tip member 72 is silver brazed to member 71 in known fashion. For surgical use, stainless steel 440-F bar stock is utilized for element 72. The shank of each tube 21, 22, member 71 here, is purchasable as a tube. The tip member 72 is purchasable as bar stock, and then bored out to its flat bottom or end wall 74.

It should be apparent that the step of heat treating is necessary in this embodiment only for tip member 72, and not the entire length of a tube 21, 22. It is the cutting edges subsequently formed about their corresponding openings 25, 45 which require a particular degree of hardness for severing tissue, and other substances involved in surgical operations on the body, whereas the shanks of tubes 21, 22 are not involved directly in surgical cutting.

The invention is also applicable to tubes 21, 22 which are not the result of an assembly of tip and shank members for each of such tubes.

What we claim as patentably distinct is:

1. A surgical instrument cutting tube comprising
    a body formation forming an opening extending into a distal end wall having an interior surface and into an annular wall forming said tube,
    a bearing surface included in the interior surface of said distal end wall and about the axis of said tube,
    the body formation for the opening in said distal end wall comprising a pair of circularly-formed radiused-cut cutting edges having contiguous extemities joined together at a protrusion of said bearing surface between the tube's axis and the opening in said annular wall,
    the body formation for the opening in said annular wall comprising a pair of spaced parallel radiused-cut cutting edges longitudinally disposed in said annular wall,
    said circularly-formed radiused-cut cutting edges having opposing extremities correspondingly joining said spaced parallel radiused-cut cutting edges at corresponding non-sharp junctures of said distal end and annular walls.

2. The tube of claim 1 including radiused-cut cornered edges correspondingly joining said spaced parallel radiused-cut cutting edges adjacent the end of the length of the opening in said annular wall.

3. A surgical instrument cutting tube comprising
    a body formation forming an opening extending into a distal end wall having an exterior surface and into an annular wall forming said tube,
    a bearing surface included in the exterior surface of said distal end wall and about the axis of said tube,
    the body formation for the opening in said distal end wall comprising a pair of circularly-formed straight cut cutting edges having their contiguous extremities joined together at a protrusion of said bearing surface between the tube's axis and the opening in said annular wall,
    the body formation for the opening in said annular wall comprising a pair of spaced arcuately-formed radiused-cut cutting edges,
    said circularly-formed straight cut cutting edges having opposing extremities correspondingly joining said spaced arcuately-formed radiused-cut cutting edges at corresponding sharp junctures of said distal end and annular walls.

4. The tube of claim 3 including an edge circumferentially disposed and flowing into corresponding arcuately-formed radiused-cut cutting edges therein.

5. A surgical instrument comprising
    co-axially assembled inner and outer tubes each having an axis,
    a body formation in each of said tubes forming an opening extending into a distal end wall and into an annular wall forming each of said tubes,
    bearing surfaces included in the distal end walls of said tubes and engaging each other and including corresponding bearing protrusions between their respective axes and respective openings in their annular walls when the opening in one tube registers with the opening in the other tube,
    the body formation about the opening in the outer tubes's distal end wall comprising a pair of circularly-formed radiused cut cutting edges having contiguous extremities joined together at its corresponding bearing protrusion,
    the body formation about the opening in the outer tube's annular wall comprising a pair of spaced parallel radiused-cut cutting edges longitudinally disposed in its annular wall,
    said circularly-formed radiused-cut cutting edges having opposing extremities correspondingly joining said parallel radiused-cut cutting edges at a corresponding non-sharp juncture of said distal end and annular walls,
    the body formation for the opening in the inner tube's distal end wall comprising a pair of circularly-formed straight cut cutting edges having their contiguous extremities joined together at its corresponding bearing protrusion,
    the body formation for the opening in the inner tube's annular wall comprising a pair of spaced arcuately-formed radiused-cut cutting edges,
    the inner tube's circularly-formed straight cut cutting edges having opposing extremities correspondingly joining its arcuately-formed radiused-cut cutting edges at a sharp juncture of said distal end and annular wall.

6. The surgical instrument of claim 5 including
    an edge circumferentially disposed and flowing into corresponding arcuately-formed radiused-cut cutting edges in said inner tube, and
    radiused-cut cornered edges correspondingly joining said spaced parallel radiused-cut cutting edges in said outer tube at the end of the length of its opening in its annular wall,
    said circumferentially disposed edge being beyond the end of the length of the outer tube's opening in its annular wall.

* * * * *